US008859264B2

(12) United States Patent
Bert et al.

(10) Patent No.: US 8,859,264 B2
(45) Date of Patent: Oct. 14, 2014

(54) PHANTOM FOR THE EXPERIMENTAL IN-VITRO VALIDATION OF RADIATION PROCEDURES UNDER THE INFLUENCE OF MOTION, TAKING INTO ACCOUNT THE BIOLOGICAL EFFECTIVE DOSE

(75) Inventors: Christoph Bert, Aschaffenburg (DE); Eike Rietzel, Weiterstadt (DE); Alexander Gemmel, Mainz (DE)

(73) Assignee: GSI Helmholtzzentrum fuer Schwerionenforschung GmbH, Darmstadt (DE)

( * ) Notice: Subject to any disclaimer, the term of this patent is extended or adjusted under 35 U.S.C. 154(b) by 1169 days.

(21) Appl. No.: 12/511,715

(22) Filed: Jul. 29, 2009

(65) Prior Publication Data
US 2011/0027853 A1 Feb. 3, 2011

(51) Int. Cl.
*C12M 1/34* (2006.01)
*A61N 5/10* (2006.01)

(52) U.S. Cl.
CPC ....... *A61N 5/1048* (2013.01); *A61N 2005/1076* (2013.01); *A61N 2005/1087* (2013.01); *A61N 2005/1072* (2013.01)
USPC .................. 435/287.1; 435/287.3; 435/288.1; 435/288.2; 435/288.3; 378/1; 378/18

(58) Field of Classification Search
None
See application file for complete search history.

(56) References Cited

U.S. PATENT DOCUMENTS

| | | | |
|---|---|---|---|
| 6,719,449 B1 * | 4/2004 | Laugharn et al. | 366/127 |
| 2003/0013188 A1 * | 1/2003 | Dumas | 435/288.4 |
| 2007/0099294 A1 * | 5/2007 | Yang et al. | 435/299.1 |
| 2008/0014571 A1 * | 1/2008 | Teich et al. | 435/4 |
| 2010/0301235 A1 | 12/2010 | Bert | |

FOREIGN PATENT DOCUMENTS

DE 102007045879 A1 4/2009
WO 2009040117 A1 4/2009

OTHER PUBLICATIONS

Hillman, GG et al. Genistein potentiates the radiation effect on prostate carcinoma cells. Clinical Cancer Research. Feb. 2001. 7: 382-390.*
Wouters, BG et al. Measurements of relative biological effectiveness of the 70 MeV proton beam at TRIUMF using Chinese hamster V79 cells and the high-precision cell sorter assay. Radiation Research. 1996. 146: 159-170.*
Bert, C et al. Target motion tracking with a scanned particle beam. Medical Physics. Dec. 2007. 34(12): 4768-4771.*
Gemmel, A et al. Biological dose optimization with multiple ion fields. Physics in Medicine and Biology. 2008. Published Nov. 12, 2008. 53: 6991-7012.*
S.O. Grötzinger, "Volume Conformal Irradiation of Moving Target Volumes with scanned ion beams," Technical University of Darmstadt, Germany, 2004, 191 pages.
C. Bert, "Bestrahlungsplan für bewegte Zielvolumina in der Tumortherapie mit gescanntem Kohlenstoffstrahl," (Radiation plan for moving target volumes in tumor therapy with a scanned ion beam), Technical University of Darmstadt, Germany, 2006, 135 pages.

* cited by examiner

*Primary Examiner* — Allison Ford
*Assistant Examiner* — Susan E Fernandez
(74) *Attorney, Agent, or Firm* — Leydig, Voit & Mayer, Ltd.

(57) ABSTRACT

A phantom device for in-vitro validation of radiation procedures under motion influence in consideration of an effective biological dose includes a phantom having a first biological detector with a first biological sample. The first biological sample includes a plurality of culturing and irradiation elements. Each of the culturing and irradiation elements are provided with a respective biological sub-sample so that the first biological detector is configured as a spatially resolving biological detector. A first motion device is configured to move the first biological detector so as to simulate a motion of a target volume.

5 Claims, 8 Drawing Sheets

PHANTOM FOR THE EXPERIMENTAL IN-VITRO VALIDATION OF RADIATION PROCEDURES UNDER THE INFLUENCE OF MOTION, TAKING INTO ACCOUNT THE BIOLOGICAL EFFECTIVE DOSE

FIELD

The present invention relates to a phantom for the experimental in-vitro validation of radiation procedures under the influence of motion, taking into account the biologically effective dose, especially for therapeutic radiation procedures using a particle-therapy accelerator. The present invention also relates to a phantom device with such a phantom and with one or more motion devices and to an appertaining method for the validation of the radiation procedures under the influence of motion.

BACKGROUND

The treatment of tumors generally involves operative resections, radiation therapy and chemotherapy, or else a combination of these methods. In the case of radiation therapy, the objective of the treatment is to apply a high, localized dose to the tumor with the least possible detrimental impact on the surrounding normal tissue. For this purpose, the energy or dose deposition of the radiation is adapted as closely as possible to the tumor. Recently, good therapeutic outcomes have been achieved with radiation with ions instead of photons since the energy or dose deposition has a sharp maximum (so-called Bragg peak) as a function of the penetration depth. In a generally known method, the beam is applied with passive beam formation components (among others, scatter films, modulators, collimators, compensators). As an alternative, however, it is also possible to focus the ion beam precisely and to scan the tumor three-dimensionally with a needle-fine beam, a so-called "pencil beam" (raster scan method, spot scan method, continuous scan method). In the raster scan method, the beam remains on one raster position for a defined number of particles and is kept switched on while it is changed to the next raster position. In the spot scan method, the beam is switched off between the raster positions, and with the continuous scan method, the beam is moved continuously at an optimized solenoid current sequence over the raster positions without stopping on them. Aside from protons, ions of the second period of the periodic table, especially carbon ions, are currently used. At times, neon ions are also employed. The use of these ions is characterized by a relative biological effectiveness (RBE) that is greater than that of photons and also of protons when it comes to the inactivation of cells. Due to their dependence on the dose level, on the type of tissue and, above all, on the particle type and particle energy, the relative biological effectiveness of the ions yields an additional therapeutic benefit in the area of the tumor.

In recent years, considerable clinical success has been achieved with radiation procedures using the raster scan method with carbon ions and dedicated radiation planning. The advantages of this method are the virtual elimination of absorber materials in order to avoid the generation of secondary particles and, above all, the good conformity of the generated dose distributions, especially proximally to the tumor. Initially, such treatment was used mainly for tumors in the region of the base of the skull and along the spinal column whose motion can be reduced to a negligible minimum through stereotactic fixation. With the planned broader clinical application of the raster scan method in various therapy centers, however, other tumors are also going to be irradiated with carbon ion beams using the raster scan method. Tumors in the torso region of the body, however, are subject to more motion, especially due to the breathing or sometimes even due to the heartbeat of the patient, causing the entire rib cage to move and change shape. When moving tumors or, in general, moving target volumes are treated using the raster scan method, one is faced with the challenge that this motion can have a detrimental effect on the homogeneity of the energy deposition of the carbon ions in the tissue. Experiments with phantoms have shown that, when a beam is applied by means of scanning, overdoses and underdoses can occur in the target volume, so that a simple enlargement of the target volume by the magnitude of the motion, as is employed in the case of passive beam application, does not allow optimal treatment.

In order to correct the influence of the motion when a beam is applied by means of scanning, at the present time, irradiation making use of safety margins, multifold radiation, interrupted radiation, motion-compensated radiation or combinations of these cited methods is being studied and used in preclinical trials. During the motion-compensated irradiation, the beam position is continuously adapted to the motion of the tumor. Here, the beam position laterally to the beam direction, and, if applicable, the particle range are continuously adapted to the motion of the tumor. In this context, mention is made of the dissertations by S. O. Grötzinger, "Volume Conformal Irradiation of Moving Target Volumes with scanned ion beams," Technical University of Darmstadt, Germany, 2004, and by C. Bert, "Bestrahlungsplan für bewegte Zielvolumina in der Tumortherapie mit gescanntem Kohlenstoffstrahl," (Radiation plan for moving target volumes in tumor therapy with a scanned ion beam), Technical University of Darmstadt, Germany, 2006, both of which are hereby incorporated in their entirety by reference herein. In any case, the motion-compensated raster scan ion beam application is fundamentally known to the person skilled in the art working in the field of particle-beam tumor therapy.

The cited dissertations, however, deal mainly with the physical energy deposition of the ion beams and did not take the greater biological effectiveness into consideration.

German patent application DE 10 2007 045 879 of Siemens AG and of the applicant, which is hereby incorporated in its entirety by reference herein, describes a method and a device for the irradiation of moving target volumes.

SUMMARY

In an embodiment, the present invention provides a phantom device for the experimental in-vitro validation of radiation procedures under motion influence in consideration of a relative biological effectiveness-weighted dose. The phantom device includes a phantom having a first biological detector with a first biological sample. The first biological sample includes a plurality of culturing and irradiation elements. Each of the culturing and irradiation elements is provided with a respective biological sub-sample so that the first biological detector is configured as a spatially resolving biological detector. A first motion device is configured to move the first biological detector so as to simulate a motion of a target volume.

BRIEF DESCRIPTION OF THE DRAWINGS

The foregoing and other features of the present invention will be more readily apparent from the following detailed description and drawings of illustrative embodiments of the invention in which.

In the Figures, identical and similar elements are at times provided with the same reference numerals, and the features of the various embodiments can be combined with each other.

DETAILED DESCRIPTION

Figure 1:
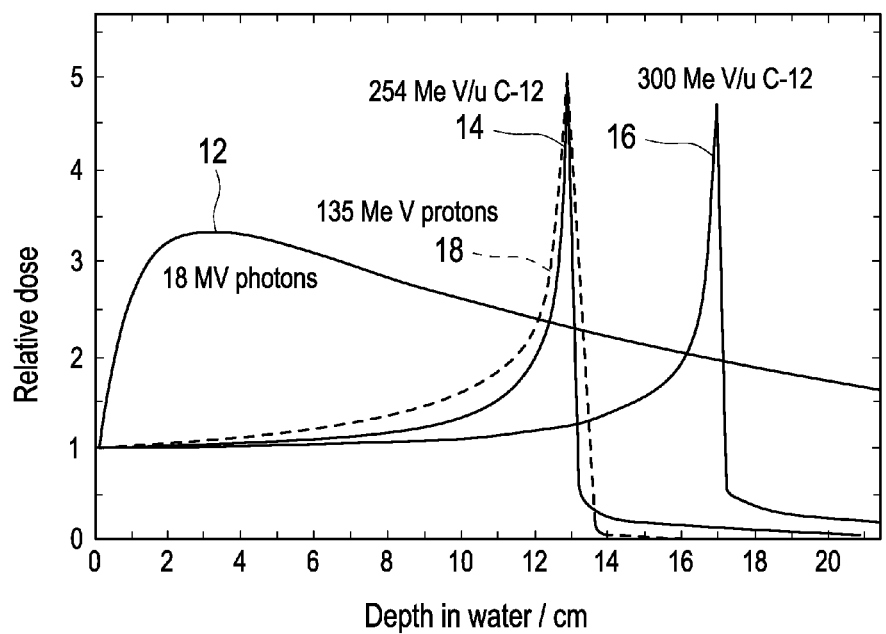
FIG. 1 is a diagram of the relative dose as a function of the penetration depth for various beam types and beam energies.

In an embodiment, the present invention provides enhanced safety, reliability and quality to improve therapy planning for moving target volumes when particle beams are used for scanning. A phantom or a phantom device and a method are provided with which quality assurance and validation of the particle-beam tumor therapy can be achieved with tumors that are moving during the irradiation.

In an embodiment, the present invention achieves a high-quality and precise validation of the algorithm for calculating the biologically effective dose in the radiation planning of the particle-beam tumor therapy, also for tumors in the thorax region.

Additionally, according to an embodiment, the present invention improves the radiation planning of the particle-beam tumor therapy with the motion-compensated scanning method.

Further, according to an embodiment, the present invention validates the motion-compensation system of the particle-beam tumor therapy.

According to an embodiment of the present invention, a phantom device is provided for purposes of the experimental validation of radiation procedures under the influence of motion, taking into account the biologically effective dose, especially for therapeutic radiation procedures. In this manner, among other things, the calculation of the biologically effective dose, i.e. the calculation of the so-called RBE-weighted dose (RBE=relative biological effectiveness) can be validated in the radiation planning for therapeutic radiation procedures using an energetic beam and involving a target volume in a living body. The validation is carried out in-vitro, that is to say, in a phantom, that simulates a living biological body, i.e. a patient with living test cells (human or animal) that is to undergo radiation.

This especially relates to the particle therapy of tumors, i.e. the energetic beam is especially a particle beam. The particles are preferably ions, currently especially carbon ions, neon ions or protons, but they can also be other particles such as, for example, other ions, antiprotons, pions or other hadrons. Therefore, this is sometimes also referred to as ion therapy or hadron therapy. The phantom device is thus positioned at the treatment site of a particle-therapy accelerator of the type currently being set up at the University Clinic in Heidelberg (Heidelberg ion beam therapy), and the radiation procedure is carried out there in order to validate the entire treatment chain. Here, depending on the requirements of the radiation plan that was drawn up during the preparation phase, it is possible to validate the time-resolved computer tomography (4D-CT) or time-resolved magnetic resonance tomography (4D-MRT), the radiation procedure itself, methods for reducing the influence of the motion and/or the algorithms for calculating the RBE-weighted dose.

The phantom device comprises a phantom that is to be irradiated, which comprises a first biological dose detector with a first biological specimen for culturing adherently growing cells. The first biological specimen, in turn, has a plurality of culturing and irradiation elements, e.g. wells of a microtiter plate, each with separate biological cell cultures, so that a plurality of separate cell cultures can be cultured and irradiated on the first biological specimen, and subsequently the survival rate of every single culturing and irradiation element can be determined for each of the cell cultures, independently of each other. The biological specimen can likewise comprise tissue samples that are a conglomeration of cell cultures. The individual tissue specimens are arranged here in a matrix structure, for example, like a chessboard. Thus, the first biological detector is configured as a spatially resolving biological detector, whereby each culturing and irradiation element forms a "biological detector pixel" so to speak, and the survival rate of the cell cultures can be evaluated separately for each biological detector pixel. For this purpose, the cell cultures are removed from the biological specimen after the irradiation and further processed in a manner that is fundamentally known to the person skilled in the art.

The phantom device also comprises a first motion device for the first biological detector by means of which the first biological detector can be moved along a predefined trajectory in order to use the phantom to simulate the motion of the target volume. In other words, a region of the first biological detector represents the target volume that is to be irradiated, thus the volume in which the Bragg peak is set, i.e. especially a tumor that is to be irradiated. The first biological detector can be moved, especially transversally, at an adjustable, three-dimensional amplitude and/or period and/or motion phase at the beginning of the irradiation. Here, the amplitude and/or the period of the motion of the phantom preferably correspond approximately to the heartbeat or breathing rate of the patient who is to undergo radiation, so as to make the simulation as realistic as possible. However, the motion can also be executed along a non-cyclical trajectory, e.g. by a robot. In this manner, for example, the so-called "baseline drift" can be studied.

Preferably, the phantom device also comprises a transversally non-homogeneous first absorber in front of the first biological detector, i.e. beam-upstream from the first biological detector relative to the ion beam. The first absorber is moved by means of a second motion device along a predefined trajectory, especially independently of the first biological detector. In particular, the first absorber is moved transversally, optionally at an adjustable amplitude, initial phase and period. The motion of the transversally non-homogeneous first absorber brings about a change or modulation in the particle energy, so that the phantom simulates different penetration depths, that is to say, the change of the longitudinal position of the Bragg peak due to different beam trajectories, in the tissue that is in front of the target volume. Thus, the biological effects can also be studied in case of a longitudinal drift of the Bragg peak at different depths with correspondingly different particle spectra.

In particular, the motions of the first biological detector and of the first absorber can be set independently of each other so that, for example, different periods and/or a phase shift can be selected in order to simulate a given motion and radiation situation as accurately as possible. The first absorber can be produced patient-specifically, if this is desired. It should be pointed out that the first absorber belongs to the phantom and thus, in addition to the optionally employed energy-modulating wedge system of the particle-therapy accelerator, it is provided in order to compensate for range changes or in order to scan the tumor in the longitudinal direction. The first absorber is arranged beam-downstream in the energy-modulating wedge system of the particle-therapy accelerator and allows energy modulation independently of the energy-modulating wedge system of the particle-therapy accelerator. In one embodiment, the motion of the first absorber can be superimposed onto the motion of the energy-modulating system, so that one hardware component is sufficient for implementing the range change.

If desired, the motions of the first biological detector and of the first absorber can have different directions, e.g. periodical oscillations along non-parallel axes. It has, in fact, been found that the motion of lung tumors during breathing tend to be aligned with the motion of the diaphragm, i.e. to have a cranial/caudal component. The motion of the anterior tissue, that is to say, especially the ribs and the interstitial rib tissue, has a ventral/dorsal motion component in addition to the cranial/caudal component.

According to a preferred embodiment of the invention, the first absorber comprises several areas having a higher beam absorption capacity between which there is material having a lower beam absorption capacity. These areas can be elongated or rod-like in shape. The first absorber is structured accordingly, especially structured periodically. This can be achieved, for example, by rods that are incorporated into a material block having a low absorption capacity. In this context, the rods having the higher absorption capacity are adapted to human or animal bones and the material inbetween is adapted to the lower absorption capacity of human or animal flesh between the ribs, so that the area in the patient's thorax between the surface of the rib cage and the lung can be simulated, that is to say, the area where the ribs, among other things, are located. Such an absorber can be used, for example, to simulate the irradiation of postcostal tumors, for example, lung tumors, in which the longitudinal position of the Bragg peak can fluctuate, depending on whether the beam, for instance, passes through a rib in the inhaled state, and passes between the ribs in the exhaled state.

Also preferably, the phantom device comprises a second biological detector with a second biological specimen, whereby the second biological detector is moved transversally by means of a third motion device with a predefined trajectory, e.g. at a predefined amplitude and period, and whereby the motions of the first and second biological detectors can be set independently of each other. Thus, the first and second biological detectors can be moved relative to each other, so that, in an advantageous manner, different motions can be simulated within the body that is to undergo radiation. Thus, for example, a lung tumor whose tissue is simulated by the second biological detector can move differently during breathing than normal tissue located in the beam path anterior to the tumor. Therefore, with this embodiment, cells that represent, for example, the normal tissue anterior to the tumor, i.e. in the plateau region before the Bragg peak of the relative dose distribution, can be irradiated simultaneously in the first biological detector, and cells that represent the tumor, i.e. in the Bragg peak, can be irradiated in the second biological detector, and subsequently the survival rates can be determined separately from each other, that is to say, in a depth-resolved manner. An application for this is, for example, the following sequence relative to the ion beam: i) organ at risk (OAR) in the entry channel, ii) the tumor and iii) another OAR distal from the tumor, e.g. the heart or mediastinum, in order to simulate such an organ/tissue sequence.

Preferably, the first and/or the second biological detector each comprise a container into which fluid can be filled, especially nutrient medium or nutrient solution for the living cells or for the tissue. The first and second biological detectors thus comprise separate containers. The first and second biological specimens are placed into the first or second container into the applicable nutrient medium. This is especially advantageous if, for example, different cell systems having different beam sensitivity levels are present in the first and second biological detectors. The nutrient media can be adapted to the specific living cells and/or other radiation elements, that is to say, they can also be different. If applicable, a third biological detector with a third biological specimen can also be provided in a third container holding nutrient medium.

In this manner, different cell types can be simulated with different nutrient media, e.g. skin in the entry channel, normal tissue in the dose plateau and tumor tissue in the target volume (Bragg peak). Moreover, different oxygenation levels can be established in the containers, for example, in order to simulate predefined hypoxic conditions in the tumor tissue, but not in the other tissue. Furthermore, different cell cycles can be used in the various biological detectors. Hence, in general, the first and the second biological detectors can contain different cell systems.

Furthermore, there is preferably a second transversal non-homogeneous absorber as well as a fourth motion device, whereby the first absorber, the first biological detector, the second absorber and the second biological detector are arranged one after the other. The second absorber can be moved transversally by means of the fourth motion device at a predefined amplitude and period, whereby the periodical motions of the two biological detectors and of the two absorbers can be controlled independently of each other.

Moreover, in an embodiment, the present invention also includes a rotation device, by means of which the phantom can be rotated at a predefined amplitude, initial phase and period around an axis crosswise to the direction of the energetic beam. This allows a motion of the phantom that comprises a periodical change in the angle of irradiation into the target volume. This can be advantageous if rotatory motion components that can be caused, for example, by the breathing, are to be simulated. On the other hand, a simple rotation of the phantom can also be used to carry out multi-field radiation procedures from different directions, e.g. for iso-centric radiation procedures of the phantom.

The motion of the biological detectors and/or of the absorbers can be executed from one-dimensionally parallel all the way to six-dimensionally (three linear degrees of freedom and three rotatory degrees of freedom) in a robot-based and detector/absorber-specific manner. It is even conceivable to use deformed absorbers, e.g. deformable rubber blocks. Through the spatial resolution, dose deviations can be detected on the basis of the interaction between the scanning of the ion beam and of the target volume.

According to a preferred embodiment, the first, second and/or third biological specimens are each configured as a cell culture means in the form of a microtiter plate, each having a plurality of wells. The indentations or wells each form the culturing and irradiation elements for the biological cell cultures or the "biological detector pixels". For this purpose, the indentations or wells have a surface inside the wells that is modified for growing the cell cultures, e.g. a cell growth layer on the bottom of the wells, so that the cells can grow adherently inside these wells.

Consequently, the microtiter plates can be placed into the appertaining containers for nutrient medium in such a way that the microtiter plates extend crosswise to the direction of the energetic beam during the irradiation. Once the microtiter plates have been placed into the appertaining containers and the individual container has been filled with nutrient medium, the microtiter plates are surrounded on both sides with the appertaining nutrient medium.

Experiments have shown that it is advantageous not to close the microtiter plates but rather to leave them open when they are placed into the containers that can be filled with nutrient medium. This prevents the formation of air bubbles in the wells, which could have an uncontrolled influence on the penetration depth or on the position of the Bragg peak, especially if the biological detector in question is moved, since this could even cause the nutrient medium to spill.

In addition, more than one biological specimen, e.g. two or more microtiter plates, can be placed into the first and/or the additional containers, whereby the microtiter plates are arranged in parallel one after the other in the appertaining container, so that two or more separate cell cultures can be irradiated one after the other in the same container. Thus, each biological detector then has a spatial resolution in the longitudinal direction as well. Consequently, according to an embodiment of the present invention, validation measurements, for example, for different layers of the tumor can be carried out by means of the scan method, especially the raster scan method. As an alternative, the microtiter plates of a container can be positioned with a slight offset crosswise to the beam in order to achieve a higher spatial resolution.

If desired, different regions of the biological detector can be irradiated immediately one after the other, so that multiple measurements are possible with a single filling of the biological detector.

The phantom device preferably comprises a motion sensor that picks up the motion of the phantom, and a control device for the particle-therapy accelerator for purposes of the motion-compensated irradiation of the phantom.

The phantom device according to an embodiment of the present invention is also fundamentally suited for radiation systems that work with passive beam adaptation. However, special advantages are provided in an embodiment of the present invention in combination with the motion-compensated raster scan method, i.e. for validating the calculation of the RBE-weighted dose with this method. The motion-compensated raster scan method is fundamentally known to a person skilled in the art. "Motion-compensated" may refer to beam tracking. According to the invention, the phantom is then irradiated using the raster scan method, and the motion data of the phantom is used for the motion compensation. The motion data is preferably ascertained with at least one motion sensor and transmitted to the therapy control system or to the control device for the raster scanning of the particle-therapy accelerator for purposes of the motion-compensated irradiation of the phantom.

Therefore, for the experimental in-vitro validation of the algorithm for calculating the RBE-weighted dose, the phantom is temporarily positioned at a patient radiation site, e.g. on the patient table and irradiated there. The first and the optionally additional biological detectors as well as optionally the absorbers of the phantom are moved transversally at a predefined amplitude and period during the irradiation, so that the phantom can simulate the motion of the target volume or tumor that is to be irradiated. After the irradiation, the survival rates of the cell cultures from the culturing and irradiation elements are each determined separately, so that a spatially resolving measurement can be performed using the "biological detector pixels" and, on the basis of the survival rates of the cell cultures of the individual detector pixels, the algorithm for calculating the RBE-weighted dose of the particle-therapy accelerator is verified.

If, as is preferred, scanning with the particle beam is carried out by means of the raster scan method using the phantom, and the first biological detector is moved transversally during the scanning, the scanning movement of the beam is superimposed onto the motion of the first and the optionally additional biological detectors in the transversal direction. The same applies to the additional biological detectors and if applicable, to the absorbers. For the validation, the beam position and the number of beam particles of the raster scan beam as well as the motion of the first biological detector and, if applicable, of the additional biological detectors, that is to say, signals of the accelerator and signals of the phantom device, are all recorded in a time-resolved manner and their correlation is evaluated. For example, the phantom device can have an input for a signal of the accelerator that is synchronous to the radiation pulsation (e.g. low/high), which is recorded by the phantom device with a signal from the accelerator. However, the motion of the phantom device can also be started synchronously with the beam or else the phantom device emits a signal with which the radiation is started synchronously with the motion. By correlating the beam position and the number of beam particles with the motion data of the first biological detector, the applied radiation doses can be determined separately for each of the culturing and irradiation elements (biological detector pixels). Thus, the relative biological effectiveness (RBE) of the radiation or the so-called RBE-weighted dose under the influence of motion can be ascertained experimentally for each of the culturing and irradiation elements. Accordingly, the algorithm for calculating the RBE-weighted dose can be validated on the basis of the spatially resolved data of the measured RBE-weighted dose under the influence of motion. The validation method can be combined with the above-mentioned methods (safety margins, interrupted radiation, multiple radiation, motion compensation, combinations of the methods), especially with the motion compensation of the raster scan radiation, so that the algorithm for calculating the RBE-weighted dose can also be validated with motion compensation.

In particular, the algorithm for calculating the RBE-weighted dose can be validated in combination with three-dimensional scanning by means of the particle beam. During three-dimensional scanning, the target volume is typically rastered layer-wise, whereby each layer (so-called iso-energy layer) is rastered two-dimensionally. The depth variation in typical particle-therapy accelerators is effectuated either by the accelerator (for example, a synchrotron and/or a linear accelerator) or by a passive absorber system by means of which the particle energy and thus the penetration depth are varied (in systems with a cyclotron). In addition to this energy modulation by the particle-therapy accelerator, the phantom encompasses the transversally non-homogeneous first absorber whose transversal motion simulates the additional and—in contrast to the energy modulation by the wedge modulator system—generally undesired temporally variable influencing of the particle energy by the motion of the body, e.g. during breathing. Consequently, for the validation, the depth modulation of the raster scanning by the particle-therapy accelerator and a depth modulation by the first absorber belonging to the phantom are superimposed. In the case of passive beam adaptation, there are also the patient field-specific absorbers and collimators, which are fundamentally known to the person skilled in the art.

Thus, the target volume is preferably rastered with the particle beam, the "pencil beam", and the three-dimensional rastering is superimposed onto a transversal, optionally two-dimensional motion of the first biological detector and optionally onto an additional variation of the penetration depth by means of the first absorber belonging to the phantom. Accordingly, the motion of the first biological detector and of the first absorber brings about a three-dimensional motion of the actual target point having maximum energy deposition in the phantom in three-dimensional space to the desired target point having maximum energy deposition. Thus, the algorithm for calculating the RBE-weighted dose under the influence of a three-dimensional relative motion between the actual target point having maximum energy deposition and the phantom and the three-dimensional rastering of the target volume can be validated.

The phantom according to an embodiment of the present invention for the experimental in-vitro validation of radiation procedures under the influence of motion, taking into account the biologically effective dose, especially for therapeutic radiation procedures using a particle therapy acceleration accelerator, comprises a first biological detector with a first biological specimen, which has a plurality of culturing and irradiation elements, each with separate biological specimens, especially biological cell cultures, whereby the first biological specimen is configured as a plate having a plurality of indentations shaped like wells, whereby the wells have a surface that is modified for growing the biological specimens, especially the biological cell cultures, so that the biological specimens, especially the biological cell cultures, can grow adherently inside the wells.

FIG. 1 shows the depth dose distribution for various types of beams. In contrast to photons (curve 12) which, after a build-up effect, exhibit an exponential drop of the dose with the depth, ions exhibit a pronounced dose maximum, which is referred to as a Bragg peak or Bragg maximum, at the end of the beam range. This maximum can be shifted in terms of depth through a variation in the energy. It can be seen that the Bragg maximum is sharper for carbon ions (curves 14 and 16) than it is for protons (curve 18).

In therapeutic irradiation, tumor cells are inactivated in order to prevent further growth and reproduction of these cells. Here, it is assumed that the cell DNA (deoxyribonucleic acid) has to be damaged as effectively as possible so that the cell cannot survive. The survival probability S of a cell line after radiation at a dose D is normally described by an exponential linear square statement:

$$S = \exp(-\alpha \cdot D - \beta \cdot D^2)$$

$\alpha$ and $\beta$ are a pair of characteristic parameters for the tissue and for the beam quality, whereby the quotient $\alpha/\beta$ is a measure of the repair capability of the cell. The therapy with ions makes use of the strong dependence of the repair capability on the quality of the radiation. This is referred to as the relative biological effectiveness (RBE). The RBE is defined as the quotient of the photon dose and the absorbed dose of the ion beams that are necessary in each case to achieve the same biological effect. In general, knowledge of the physical energy dose D is not the same as knowledge of the RBE-weighted dose, although the latter is indispensable for the precise planning of the radiation, since, for example, in the worst-case scenario, an overdosing of the beam could have fatal consequences. One possibility for theoretically calculating the RBE is the local-effect model in which the size of the cell nucleus, the track structure of the ion and the cell survival curve after photon radiation are all taken into account. However, it is evident that such theoretical models contain many approximations and should be verified experimentally.

Figure 2:
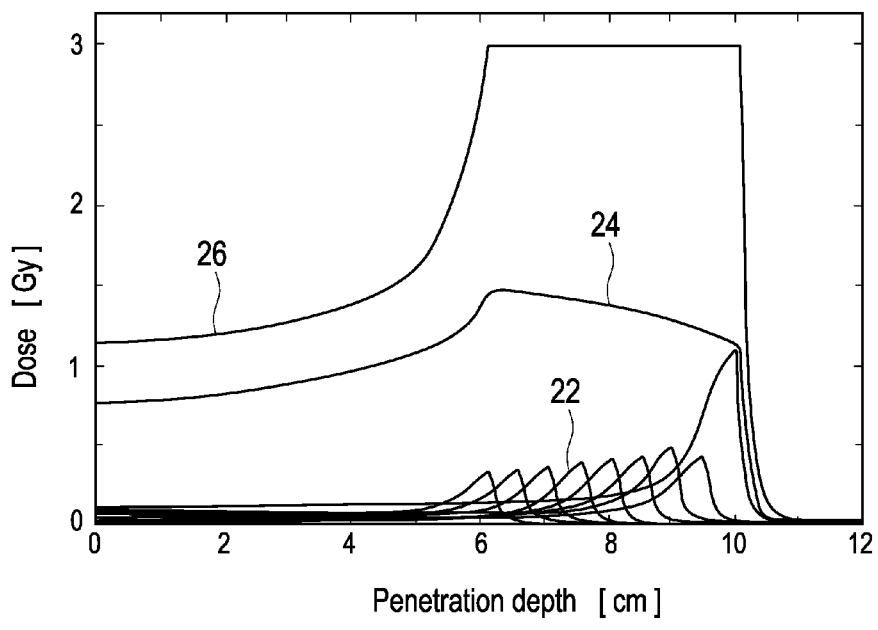
FIG. 2 is a diagram of the dose as a function of the penetration depth in contrast to the physical dose and the biologically effective dose.

FIG. 2 shows the generation of an extended Bragg peak. The superimposition of many individual beams 22 having different ranges yields a distribution of the absorbed physical dose 24. The curve 26 is an RBE-weighted dose distribution 26.

Figure 3:
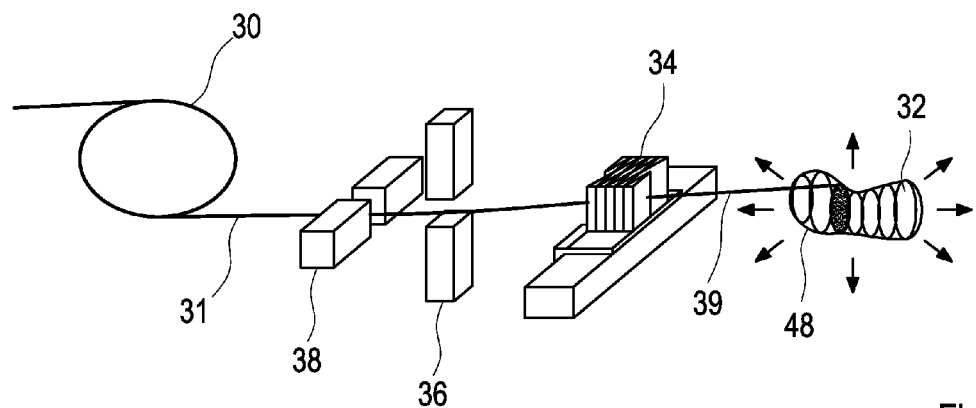
FIG. 3 is a schematic three-dimensional depiction of a radiation device with a raster scan system for a therapy irradiation system.

FIG. 3 explains the raster scan method. In the raster scan method, the ion beam 31 already provided by the accelerator 30 is used to scan a target volume 48 that is to be irradiated. The target volume 48 here is divided into iso-energy layers 32, in other words, into layers having the same particle range. For this purpose, an energy library is available, for example, at the synchrotron, comprising 252 different energies in the range from approximately 88 to 430 MeV/u, which corresponds to a water-equivalent range of approximately 2 to 32 cm at an increment width of 1 to 1.5 mm. With the raster scan method, the beam is moved within each layer one line at a time over a uniform grid of so-called raster dots. The irradiation is intensity-controlled, that is to say, once the predefined number of particles has been deposited on a raster dot, the particle beam is set to the position of the next raster dot without an interruption of the beam. On average, the irradiation takes about 10 ms for a raster dot, about 2 seconds for a layer and about 5 minutes for a fraction. The two-dimensional scanning of the iso-energy layers is carried out with two scanner magnet pairs 36, 38 that are perpendicular to each other, as is fundamentally known to the person skilled in the art. With the double-wedge modulator system 34, the depth adaptation can be achieved in conjunction with the motion compensation.

Generally speaking, the objective of the radiation planning is to optimize a set of machine parameters so as to obtain an optimal dose distribution. This includes the determination of the number of fields, their irradiation direction, the definition of the iso-energy and of the beam positions. Furthermore, this objective comprises the optimization of the number of particles per beam position on the basis of which the RBE-weighted dose distribution can be calculated, which is optimized in such a way that the tumor is destroyed while the surrounding healthy tissue is not detrimentally affected. In the case of ion therapy that scans with carbon beams, a field is defined, for example, by the position of the patient table, by the target point in the patient and by the radiation parameters of the so-called radiation plan, which contains the energies, full widths at half maximum, and beam positions (as raster dots) that are to be used. Each raster dot is defined by its iso-energy layer, by two coordinates that correspond to the horizontal and vertical deflections of the beam caused by the scanner magnets 36, 38, and by the number of particles to be deposited. A robot-controlled patient positioning and/or a gantry are likewise possible and each of these permit even more degrees of freedom.

Figure 4:
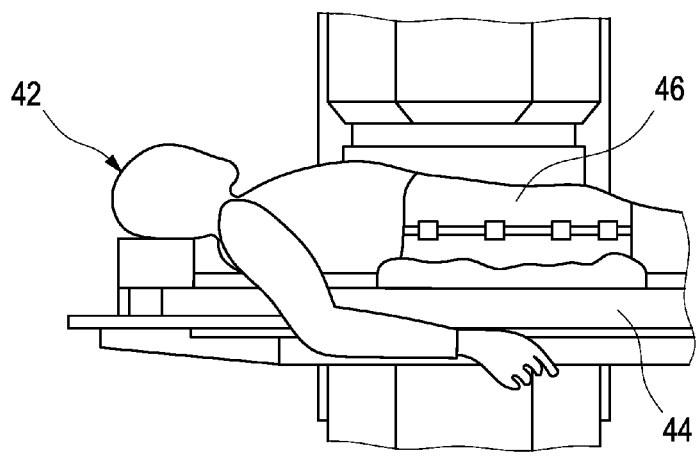
FIG. 4 is a photograph of a patient on a patient table in the radiation position.

FIG. 4 shows a patient 42 on a treatment table 44, positioned for an irradiation of the abdominal region 46. It is clear that, when the patient breathes, a relative motion between the tumor and the desired raster dot occurs, since the external fixation of the abdominal region 46 does not translate into a fixation of the internal, breathing-induced motion. Such changes in the tumor position during a fraction, i.e. motions of the patient in the range of seconds or minutes, are referred to as intra-fractional motions. In particular, these intra-fractional motions become superimposed onto the scanning movement of the beam, which can fundamentally lead to undesired, impaired conformity of the spatial dose distribution, and especially to local fluctuations. Preliminary experiments have shown that the greatest motion in the torso in humans occurs in the craniocaudal direction, namely, up to 4 cm. Moreover, it has been found that lung tumors in the lower region of the lung move considerably more than tumors in the upper region of the lung. Tumors that lie against firm structures such as the vertebrae or the thoracic wall move less. In many patients, the motion trajectory of the tumor even follows a path with hysteresis.

Various types of sensors 52 can be used to detect the motion, for example, the Real-Time-Positioning-Management (RPM) of Varian Medical Systems Inc., Palo Alto, Calif., U.S.A., the so-called Anzai belt, for example, type AZ-733V made by Anzai Medical, Tokyo, Japan, a stereo camera-based system made by Vision RT Ltd., London, England, under the name GATE RT, implanted transponders, e.g. made by Calypso Medical Technologies Inc., Seattle, Wash., U.S.A., whose position is determined in three dimensions through electromagnetic interaction, or the radiation system CYBERKNIFE made by Accuray Inc., Sunnyvale, Calif., U.S.A., with which an external motion measurement is corrected by an infrared marker with fluoroscopic data. If external motion sensors are used that are not directly part of the phantom device, then an adapter is installed on the phantom device so that the external sensors can be coupled to it. For example, a device is installed on the detector that is defined as the tumor, e.g. the second detector 66', and this device can hold the RPM box or, for instance, a spring for the Anzai sensor. This has the advantage that the motion detection that is part of the radiation device can also be validated and the phantom device is an autonomous and independent device. When it comes to the motion phantom according to an embodiment of the present invention, suitable proximity sensors include, among others, industrial sensors on the basis of triangulation (e.g. made by Sick Vertriebs GmbH, Düsseldorf, Germany OD100-35P840).

Figure 5:
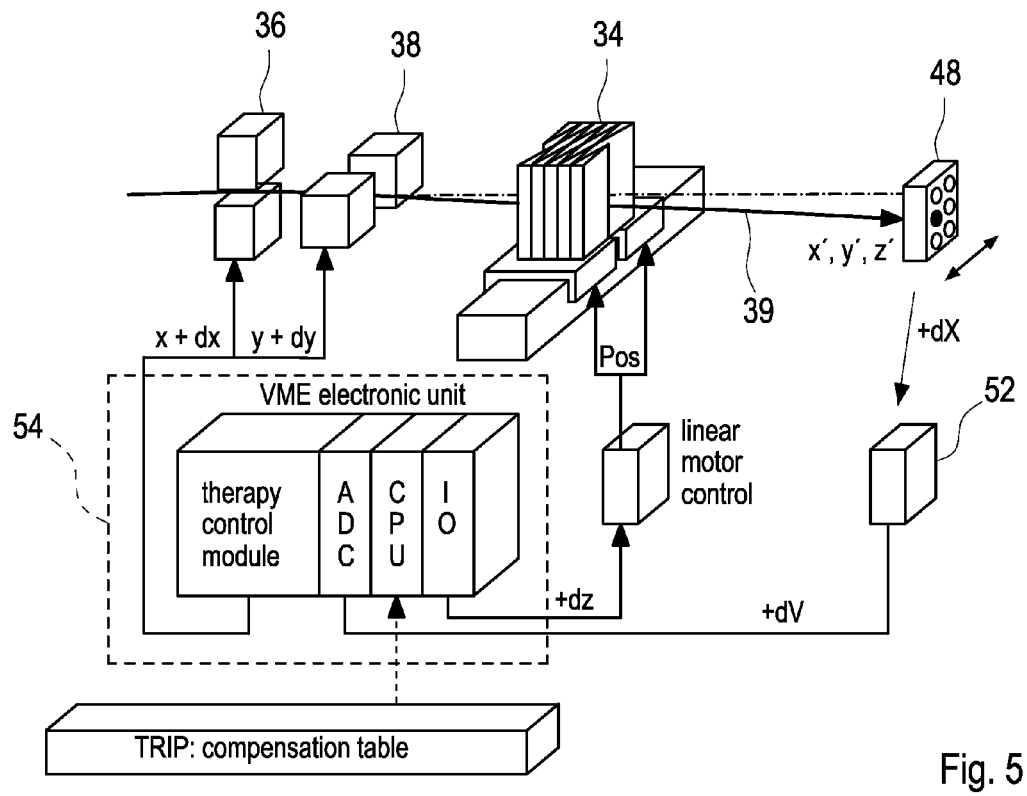
FIG. 5 is a schematic depiction of the system for motion compensation in a radiation device.

For the radiation with motion compensation, FIG. 5 schematically shows how the time-resolved position data obtained with the sensor for the position measurement 52 is fed into the therapy control system 54. By means of the fed-in time-resolved position data, the therapy control system 54 continuously performs a motion compensation by actuating the scanner magnet pairs 36, 38 and the energy modulation wedge 34, in order to actively compensate for the motion of the target volume 48. For the uninterrupted radiation, the position measuring unit 52 is used to switch the beam on and off on the basis of a radiation window prescribed by the physician. In the simplest version, no position measurement is necessary for rescanning. These methods have been comprehensively tested, but the calculation of the RBE-weighted dose, especially under the influence of motion of the target volume 48, is experimentally validated in an embodiment of the present invention.

Figure 6:
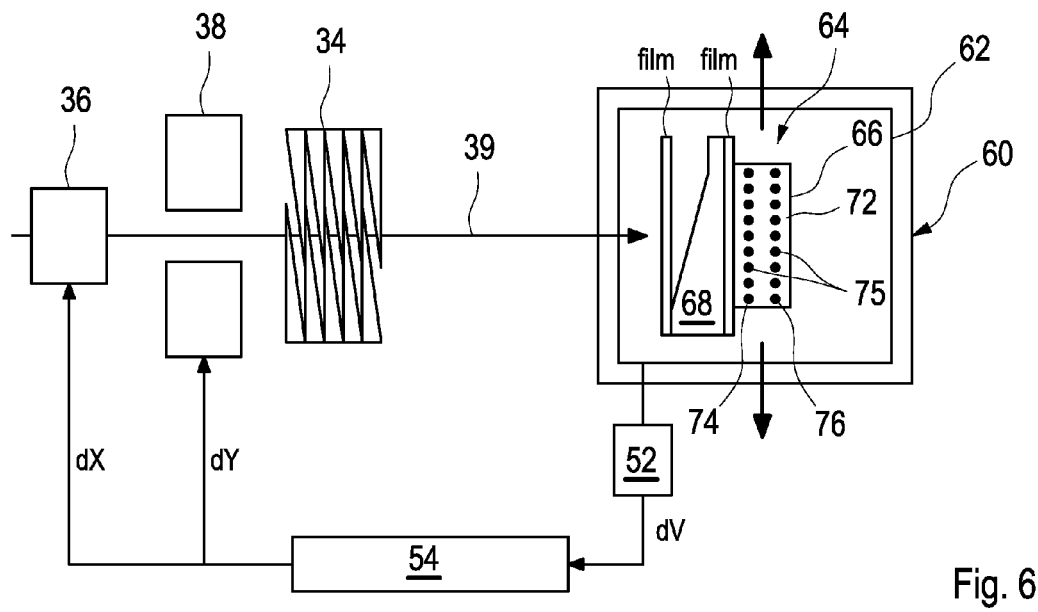
FIG. 6 is a schematic depiction of a phantom device in combination with a motion-compensated particle beam.

This is done, for example, with the phantom device 60 shown in FIG. 6. The phantom device 60 comprises a motion device in the form of a moving table 62 and a phantom 64. The phantom 64 comprises a first biological detector 66 and a transversally non-homogeneous first absorber 68, which is wedge-shaped in this example, located beam-upstream from the first biological detector 66.

Instead of being configured as an absorber wedge, the transversally non-homogeneous first absorber 68 can be configured, for example, as an absorber cascade or as a patient-field-specific absorber, which are individually milled with scattered fields, in a manner similar to compensators for ion therapy. In the embodiment shown in FIG. 6, the first biological detector 66 comprises a container 72 filled with nutrient medium, into which two microtiter plates 74, 76 have been placed in parallel one after the other. The microtiter plates 74, 76 are indicated by the dark round dots 75. However, the detector 66 can likewise contain one or more tissue samples that have a matrix-like structure, so that measuring points corresponding to the dots 75 can be recorded and analyzed.

The moving table 62 imparts the absorber 68 and the first biological detector 66 with a transversally periodical motion, for example, an oscillation, that corresponds approximately to the frequency of the breathing motion of a human. The target volume 48 in the form of the first biological detector 66 is scanned by means of the therapy control system 54 with the ion beam 39, and the laser sensor 52 detects the motion dV of the first detector 66 in a time-resolved manner in order to perform a motion compensation, which is only transversal in this example. In other embodiments, the moving table 62 can be replaced by a robot arm.

Figure 12:
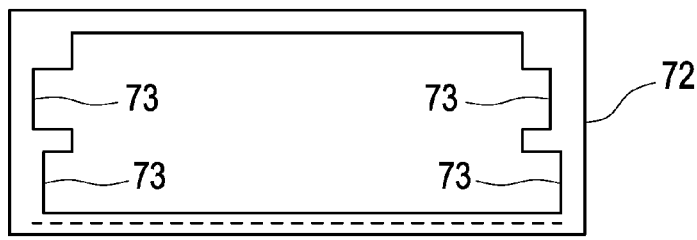
FIG. 12 is a horizontal section through a container for the biological detectors.
Figure 13:
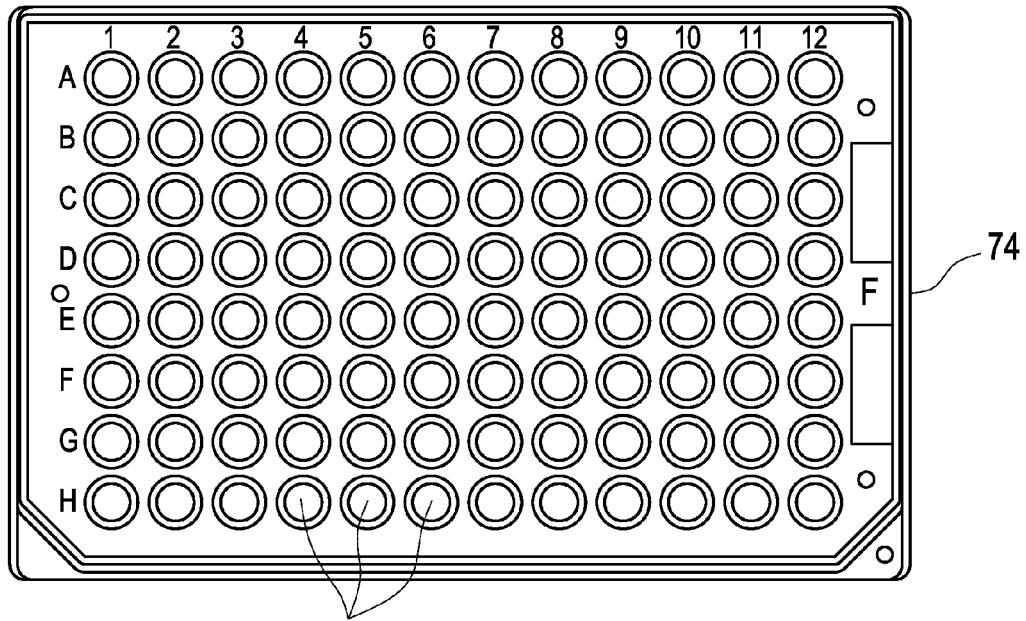
FIG. 13 is a front view of a microtiter plate to be placed into the container of FIG. 12.

The container 72 and the microtiter plates 74 and 76 are shown in greater detail in FIGS. 12 and 13. FIG. 13 shows the microtiter plate NUNC F 96 Mikrowell made by Nunc GmbH & Co. KG, which is presented by way of an example. It comprises 96 indentations or wells 78 arranged regularly in 12 columns and 8 rows. The distance from the center of a well 78 to the center of the adjacent well 78 is 9 mm in the vertical and horizontal directions. Each well 78 is conical in shape and has an opening diameter of 7 mm and a diameter of 6.2 mm at the bottom. The bottom is flat and provided with a growth layer in order to allow growth of the cells, for example, CHO cells. Consequently, each well 78 contains an independent cell specimen that corresponds to an experimental measuring point and can thus be referred to as a "biological detector pixel".

In preparation for the irradiation, sufficient cells are placed into the wells 78 and cultured accordingly. Typically, one well 78 contains tens of thousands of cells for the irradiation. After the irradiation, the survival rate of the cells is determined separately for every single well 78, thus allowing a spatially resolved determination of the survival rate of the cells.

Figure 14:
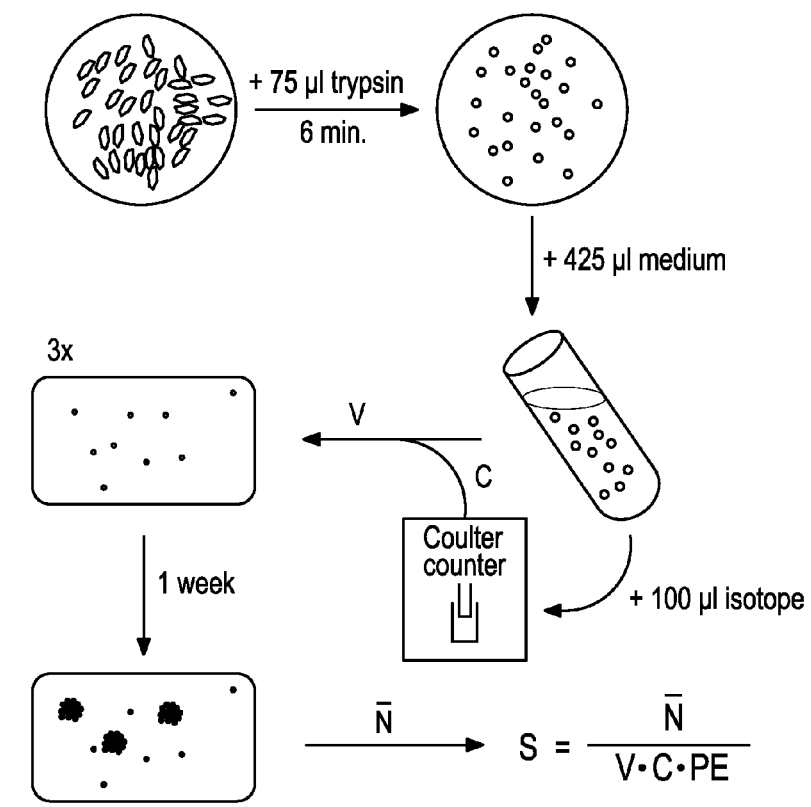
FIG. 14 is a flow chart for determining the cell survival.

FIG. 14 shows a flow chart for determining the cell survival by way of an example. First of all, the cells of a well are treated with trypsin to facilitate separation. The enzyme trypsin dissolves protein bonds and causes cell damage if the treatment is too long. The separated and individuated CHO cells are pipetted with the trypsin into a medium in order to stop the action of the trypsin. Part of the cell suspension is used to determine the cell concentration C using a Coulter counter. Depending on the cell concentration and on the expected cell survival, the volume V of the cell suspension is then placed into three T75 culture flasks with 5 ml of medium. Subsequently, the cells are stored in an incubator for one week while the cells that are capable of dividing form colonies. These colonies are then counted and this result is converted into a survival value S.

Figure 7:
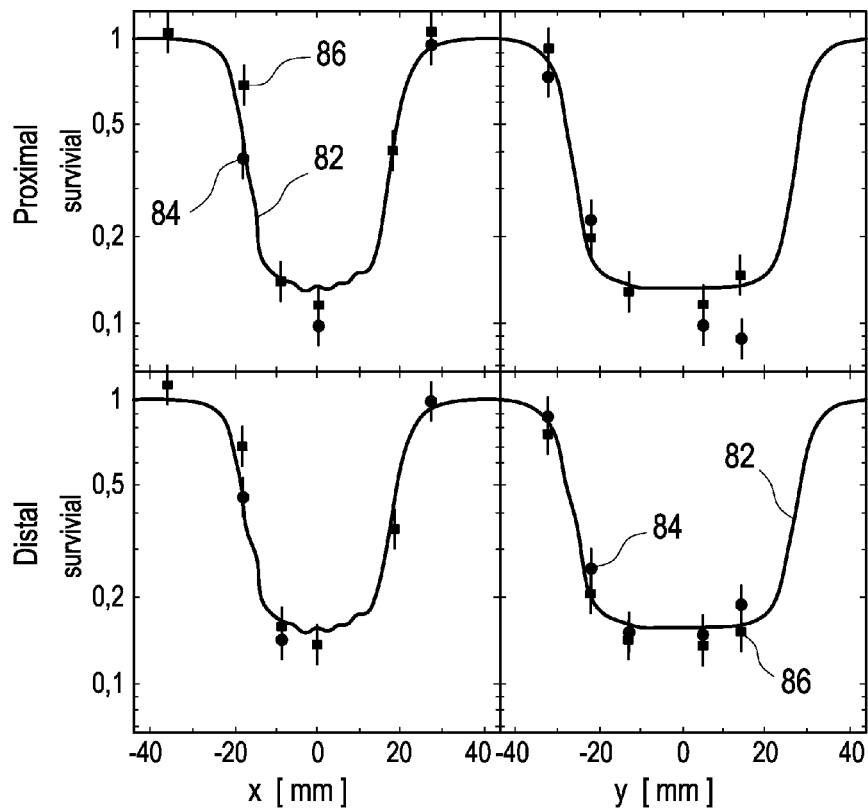
FIG. 7 is a chart of experimental results with the phantom device of FIG. 6.

FIG. 7 shows a comparison of the calculated survival rate with the experimentally determined survival rates for the validation according to the invention. The two upper graphs show the results for the anterior or proximal microtiter plate 74 and the two lower graphs for the posterior or distal microtiter plate 76. The left-hand column shows the spatial resolution in the X-direction and the right-hand column in the Y-direction. The solid line shows the calculated function 82 for the cell survival that is to be validated according to an embodiment of the present invention. The circular measuring points 84 show the stationary, experimentally measured values for the cell survival, and the square measuring points 86 show the experimentally measured values for the cell survival during motion of the phantom 64 with motion compensation. The results show a very good correlation of the experimentally determined values for the cell survival with the theoretical calculation and the proper functioning of the motion compensation. Thus, this experimental validation of the calculated values is highly advantageous for the quality of the radiation planning.

Figure 8:
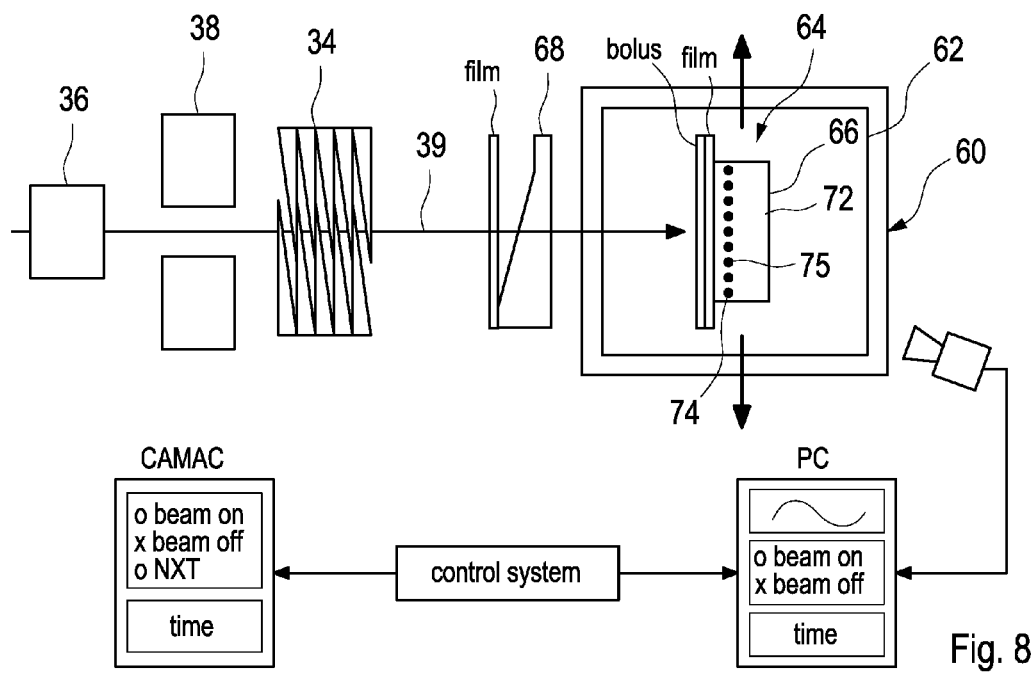
FIG. 8 is a schematic depiction of a phantom device when used without motion compensation.

FIG. 8 shows the irradiation of the phantom 64, whereby the first detector 66 is moved on the moving table 62, but not the first absorber 68, which is stationary in this example. In the example shown in FIG. 8, the validation measurement is carried out with a motion of the first detector 66, which contains only one microtiter plate 74 in this example, but was carried out without motion compensation, in order to once again show the advantages of the motion compensation in comparison to FIGS. 6 and 7, as well as to show that the experimental validation can also be used without motion compensation.

Figure 9:
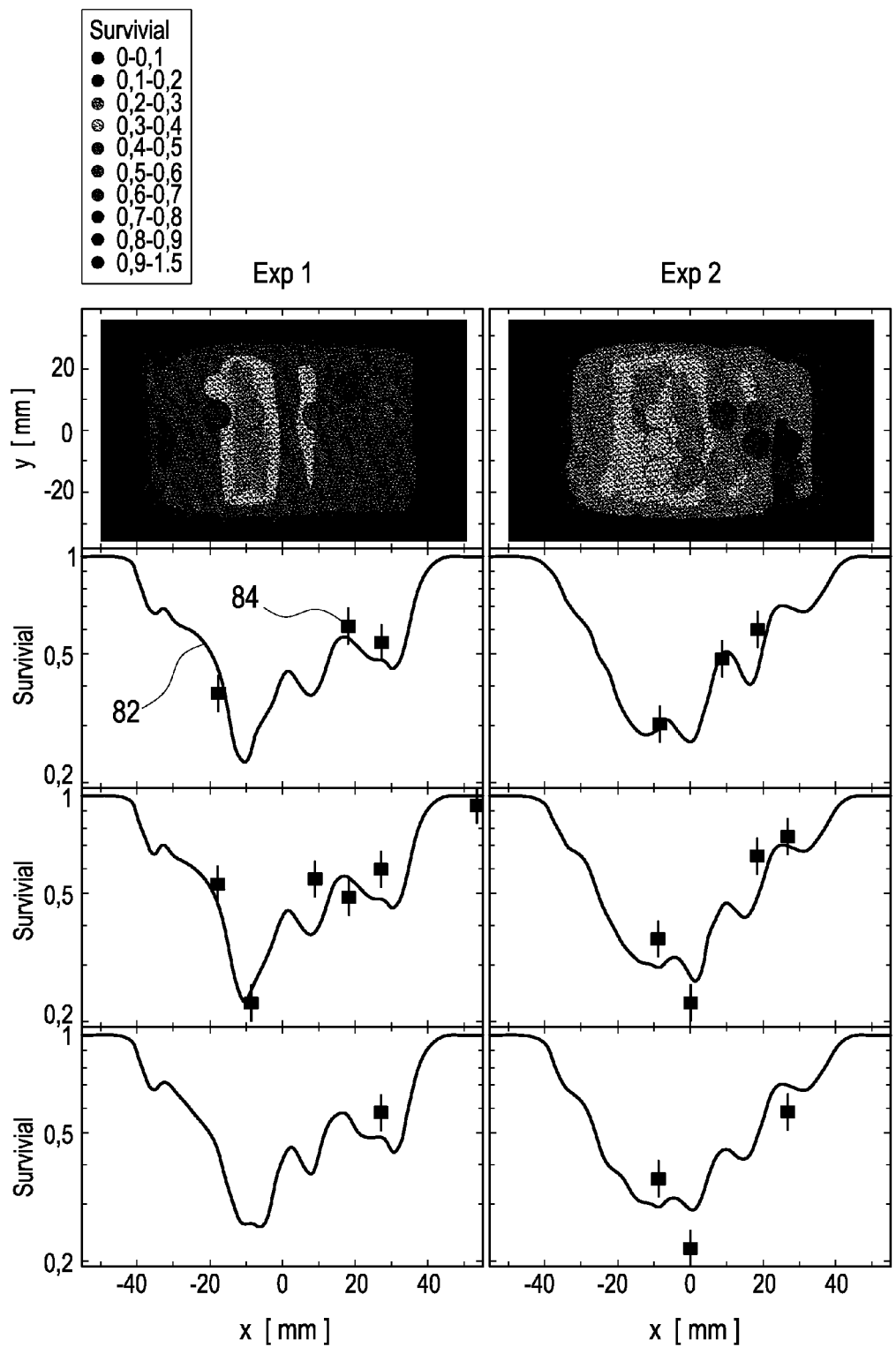
FIG. 9 is a chart of experimental results with the set-up of FIG. 8.

FIG. 9, in turn, shows the calculated curves 82 for the cell survival as well as the square experimental measured values 88 which once again exhibit a close correlation with the calculated curves. The upper row in the figure shows a two-dimensional depiction of the cell survival on the two-dimensional spatially resolving first biological detector 66, whereby the circles each represent the experimentally evaluated measuring points. The three figure rows further down in the figure represent the three rows at measuring points in the two-dimensional depictions of the upper row in the figure.

In summary, on the basis of the experiments already carried out, FIGS. 7 and 9 show that the motion phantom 64 according to the invention lends itself well for validating the employed algorithms for calculating the RBE-weighted dose under different radiation conditions and they also show that the phantom 64 is fundamentally well-suited for carrying out biological dosimetry for moving target volumes 48.

Figure 10:
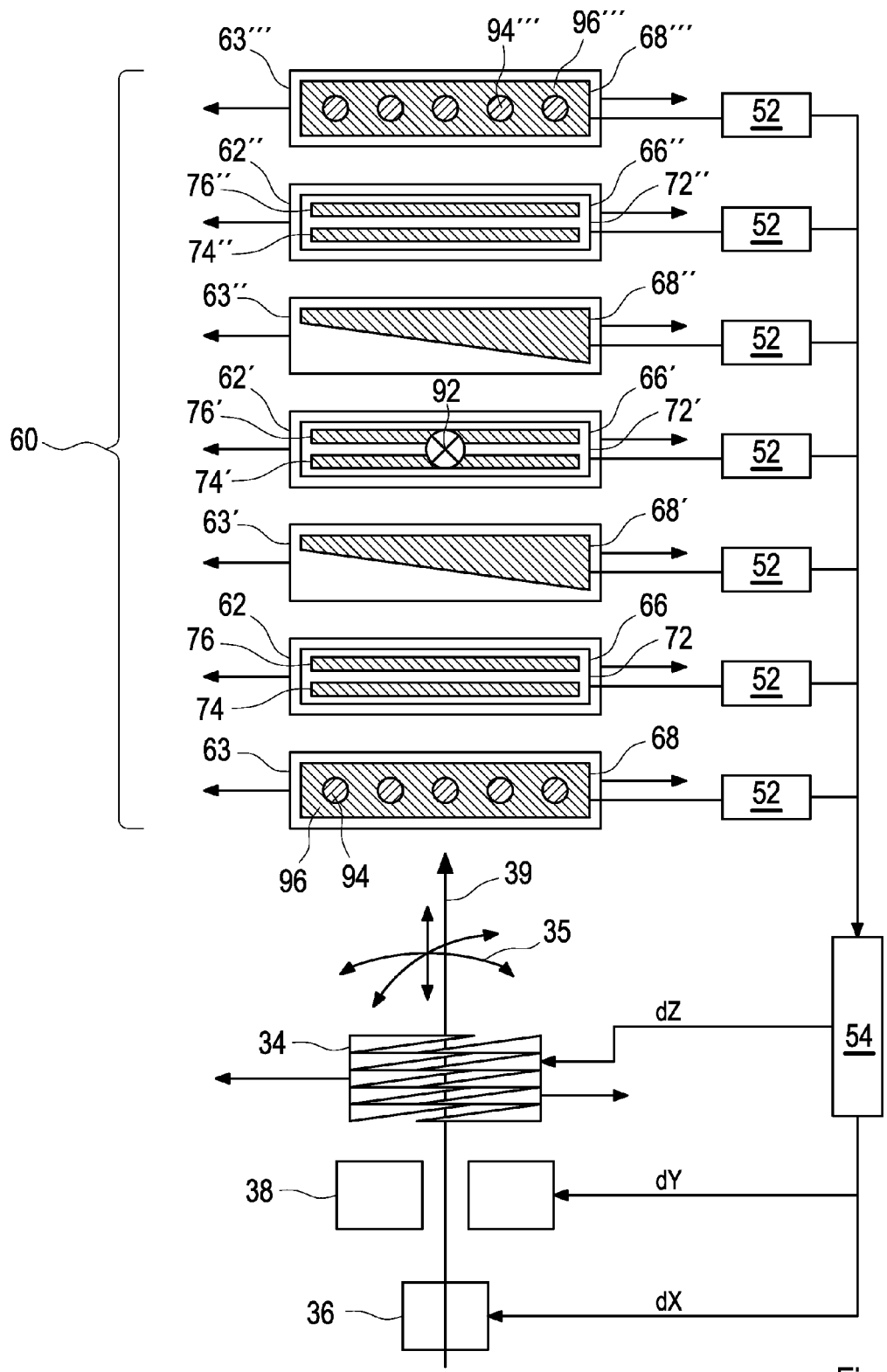
FIG. 10 is a schematic depiction of a phantom device with several biological detectors and several absorbers.

FIG. 10 shows the phantom 64 according to an embodiment of the present invention, with a plurality of spatially resolving biological detectors 66, 66', 66" and a plurality of absorbers 68, 68', 68", 68'". The phantom 64 comprises the first spatially resolving biological detector 66 with the first container 72 and with the biological specimens that are configured as microtiter plates 74 and 76. A first absorber 68 is arranged upstream from the first biological detector 66 relative to the ion beam 39, said first absorber 68, however, being configured differently from that in FIGS. 6 and 8. The phantom 64 also comprises a second and third transversally non-homogeneous absorber 68', 68"—which are each wedge-shaped in this example—and an additional absorber 68'" structured on the rear, as well as a second and third spatially resolving biological detector 66', 66". The biological detectors 66, 66', 66" each have separate containers 72, 72', 72" for placement into the appertaining microtiter plates 74, 76; 74', 76'; 74", 76". In this manner, different nutrient solutions can be filled into the different biological detectors, and different cell types and/or tissue types can be cultured. In this example, the absorbers 68, 68', 68", 68'" as well as the detectors 66, 66', 66" can all be moved independently of each other by means of independent motion devices 62, 62', 62"; 63, 63', 63", 63'", so as to achieve a highly complex, realistic motion simulation of the body that is to undergo radiation. Each absorber and detector is associated with a motion sensor 52 that uses a data acquisition system 99 to log the motion data of every single absorber and detector in a manner that is time-resolved and correlated over time with the acceleration process. This data enters into the dose calculation on the basis of which the expected survival level S per detector element is determined. In parallel, the data can be transmitted to the therapy control system 54 so that, if desired, a motion-compensated radiation or interrupted radiation as well as validation can be carried out. The therapy control system controls the three-dimensional scanning (dX, dY, dZ) through actuation of the magnet pairs 36 and 38, as well as through energy variation using the synchrotron. The three-dimensional scanning is indicated by the arrows 35. By means of the various absorbers 68, 68', 68", 68'" and/or spatially resolving biological detectors 66, 66', 66" that can be moved independently of each other, a differential motion of several tissue layers in the body of the patient can be simulated, for example, a complex motion of the tissue during breathing.

Additionally, the phantom 64 also has a rotation device with a point of rotation 92 around which the phantom 64 can be mounted so as to be rotatable. This makes it possible to irradiate two or more fields from different angles, without having to make a change to the structure of the phantom 64. For this purpose, the additional absorber 68'" is provided on the side of the first biological detector 66 opposite from the first absorber 68. Thus, the first biological detector 66, which represents the tumor that is to be irradiated, is arranged between the first absorber 68 and the additional absorber 68'", so that the first absorber 68 can simulate the ribs in front of the tumor and the additional absorber 68'" can simulate the ribs behind the tumor, or vice versa.

Figure 11:
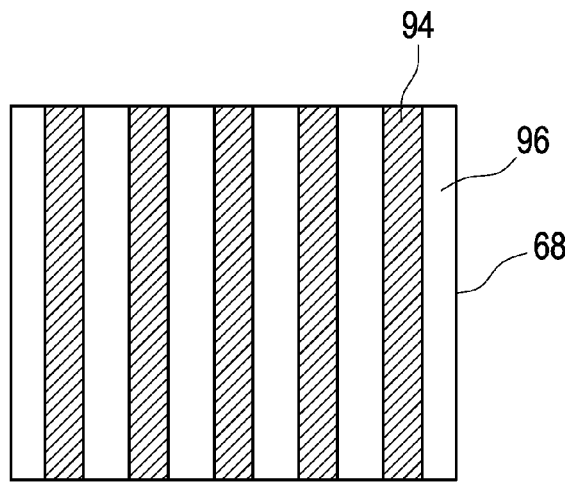
FIG. 11 is a schematic depiction of the first absorber of FIG. 10.

As shown in FIGS. 10 and 11, the first absorber 68 is internally structured. In this example, the first absorber 68 has rods 94 with a high absorption capacity, which are arranged next to each other at intervals. The rods 94 (for example, made of Teflon) are embedded in a block made of a material 96, for example, PMMA, that has a lower absorption capacity. Here, the rods 94 simulate human ribs and the material 96 between the rods simulates human tissue between the ribs. The additional absorber 68'" on the rear is structured similarly to the first absorber 68 and simulates the rear ribs. The rear absorber 68'" can have a different relationship of the distances between the rods 94'" and the interstice material 96'" than the front absorber 68. Consequently, the absorber 68 allows a relatively realistic simulation of the human rib cage in the region of the ribs.

As shown in FIG. 12, the container 72 has guide grooves 73 into which the microtiter plates 74, 76 can be inserted upright one after the other. When the microtiter plates 74, 76 are inserted, care should be taken to ensure that no air bubbles are formed in the wells 78. After the microtiter plates have been inserted, the container 72 is then filled with nutrient medium until all of the wells 78 of the microtiter plates 74, 76 that are to be irradiated have been filled with nutrient medium. The microtiter plates 74, 76 are placed into the container 72 without being closed in order to prevent the formation of air bubbles in the wells. This prevents a detrimental and indefinable influence of air bubbles on the beam range. Moreover, an interruption caused by an incorrect feed of nutrient medium can be avoided, since this could likewise falsify the results of the experiment. The container 72 allows the placement of two microtiter plates one after the other, so that not only a two-dimensionally laterally spatially resolving detector is provided, but also two measuring points are provided in the longitudinal direction one after the other. The two microtiter plates can be placed into the container 72 flush one after the other or, for example, with an offset of half a well each time. The container 72 is preferably made of PMMA, which is easy to disinfect and contains few heavy elements that could additionally scatter the ion beam.

FIG. 13 shows an example of a microtiter plate 74 with 96 wells 78 arranged in a matrix-like formation. The use of microtiter plates 74, 76 with wells 78 is especially advantageous for a moving phantom 64 since the cells grow adherently on the bottom of the wells 78 and consequently, the biological cells are also protected against excessive sloshing or flowing, even when the biological detector 66 moves.

Figure 15:
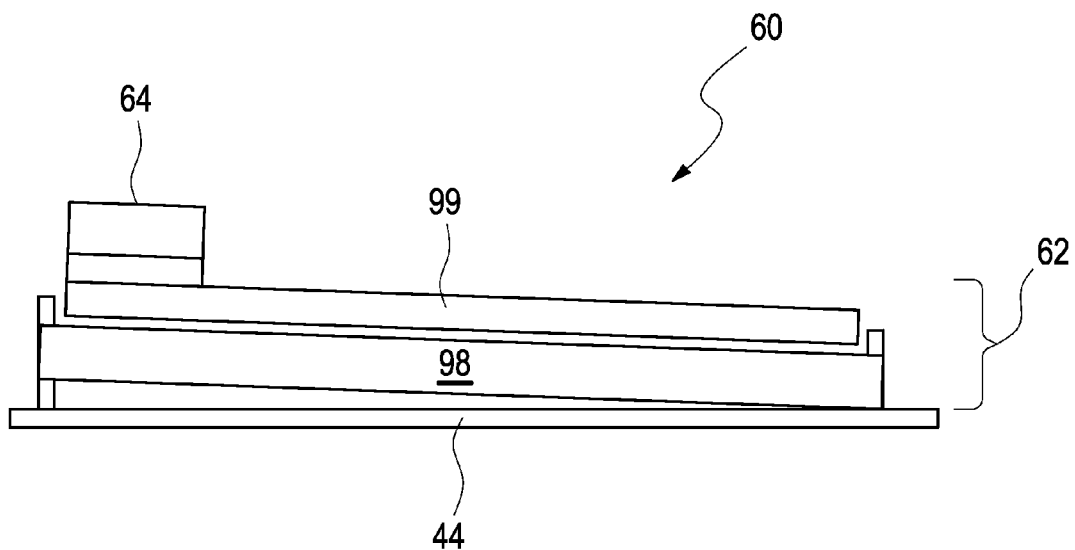
FIG. 15 is a schematic cross-sectional depiction of a motion device.

By way of an example, FIG. 15 shows the structure of a moving table 62 with a stationary platform 98 and a moveable platform 99 arranged thereupon, which are set up together on the patient table 44. The phantom 64 is set up on the moveable platform 99 so as to be moved along with the moving table 62. The structure in FIG. 15 corresponds here to the simple structure in FIG. 8.

The stationary platform 98 of the moving table 62 is made of a Trovidur panel and is slightly slanted—2.2° in this example—in order to compensate for the slant of the beam at the therapy site. The moveable platform 99, made of PMMA in this example, can carry out a one-dimensional sinusoidal motion that is brought about by a motor and transmitted via an adjustable eccentric wheel to the platform 99. The amplitude of the motion is adjustable, in this example between 1 mm and 25 mm. Moreover, the period of the motion is adjustable, in this example between 2.5 seconds and 6.5 seconds. The motion device 62 can be controlled by an external signal, so that, for instance, the motion can be started synchronously with the start of the radiation, for example, in order to establish a specific initial phase of the table.

In this example, the motion is measured with a laser sensor 52 OD 100-35P840, made by SICK Vertriebs GmbH, Düsseldorf, Germany. The laser sensor 52 is attached to the stationary plate 98 and it measures the motion of the moveable platform 99.

In summary, the invention allows biological dosimetry under the influence of motion, if applicable, with a differential motion between one or more biological detectors 66, 66', 66" and one or more absorbers 68, 68', 68", 68'''.

In particle therapy, especially with ions, which are heavier than protons, a greater biological effectiveness has to be assumed, that is to say, as a function of the dose level, of the energy and spectral composition of the particle field and of the biological system, the absorbed dose is weighted with a factor in order to describe the biologically effective dose, which in modern terminology is referred to as the RBE-weighted dose. The greater biological effect has to be taken into consideration in the radiation planning, which is done by means of complex modeling. This complex biological modeling can be validated experimentally in vitro by means of the phantom according to an embodiment of the present invention.

In an embodiment, the present invention also provides a method for the validation of therapy planning for scanned particle beams as well as a motion phantom that allows the measurement of the biological effect of the radiation in cell cultures in vitro. In particular, a method and a phantom have been developed, allowing integration into the therapy control system 54 of a particle-therapy accelerator 30 and also allowing a routine and reliable execution of experiments on cell survival, even in case of radiation with motion compensation. The motion phantom according to the invention makes it possible to test the method for the radiation of intra-fractionally moving tumors in a particle-therapy accelerator, and the algorithm for calculating the RBE-weighted dose can be validated.

It is evident to a person having ordinary skill in the art that the above-described embodiments are to be understood as examples and that the invention is not limited to them but rather, can be varied in many different ways, without departing from the scope of the invention. Furthermore, it is evident that the features, irrespective of whether they are disclosed in the description, in the claims, in the figures or elsewhere, also individually constitute integral parts of the invention, even if they have been described together with other features.

The invention claimed is:

1. A system for experimental in-vitro validation of radiation procedures under motion influence in consideration of an effective biological dose using a phantom, the system comprising:
a radiation device configured to produce a beam for the radiation procedures; and
a phantom comprising:
a first biological detector comprising a first biological sample, the first biological sample including a first microtiter plate with a plurality of culturing and irradiation elements configured as well-shaped indentations, each of the well-shaped indentations being provided with a respective biological sub-sample and having a surface adapted for growing the biological sub-samples adherently therein, and a first container for fluid configured to removably receive the first microtiter plate so that the first microtiter plate is surrounded on opposite sides by fluid when the first container is filled; and
a second biological detector having a second container for fluid configured to removably receive another microtiter plate, the first and second biological detectors including biological sub-samples from different cell systems,
wherein the first and second containers are arranged in sequence in a direction of the beam such that the beam passes through the first biological detector before passing through the second biological detector and the second biological detector is arranged behind the first biological detector.

2. The system according to claim 1, wherein the first microtiter plate disposed within the first container is not closed.

3. The system according to claim 1, wherein the first biological detector includes a second microtiter plate, and wherein the first container is configured to removably receive the first and second microtiter plates in parallel one after the other.

4. The system according to claim 1, further comprising a transversally non-homogeneous first absorber disposed before the first biological detector and a transversally non-homogeneous second absorber disposed before the second biological detector so that the first absorber, the first biological detector, the second absorber and the second biological detector are arranged in sequence in the direction of the beam for the radiation procedures.

5. The system according to claim 1, wherein the radiation procedures are therapeutic radiation procedures using a particle-therapy accelerator and the biological sub-saamples are biological cell cultures.

* * * * *